United States Patent [19]

Sheehy et al.

[11] 4,265,873

[45] May 5, 1981

[54] METHOD FOR TYPING HUMAN LEUKOCYTE ANTIGENS

[75] Inventors: Michael J. Sheehy, Madison, Wis.; Paul M. Sondel, Boston, Mass.; Fritz H. Bach; Marilyn L. Bach, both of Madison, Wis.; Rudolf Wank, New York, N.Y.

[73] Assignee: Wisconsin Alumni Research Foundation, Madison, Wis.

[21] Appl. No.: 921,487

[22] Filed: Jul. 3, 1978

Related U.S. Application Data

[63] Continuation of Ser. No. 697,545, Jun. 18, 1976, abandoned.

[51] Int. Cl.³ .................... G01N 33/16; A61K 43/00
[52] U.S. Cl. ........................................ 424/1; 435/7; 435/34
[58] Field of Search ............... 424/1, 1.5, 11, 12; 195/1.8, 103.7; 23/230 B, 230.3

[56] References Cited

U.S. PATENT DOCUMENTS 3,900,461    8/1975    Wilson et al. .................. 195/1.8 X

OTHER PUBLICATIONS

Bach, Radioisotopes in Medicine: In Vitro Studies, U.S. Atomic Energy Commission, Jun. 1968, pp. 579–588.
Hirschberg et al., Chemical Abstracts, vol. 80, No. 21, May 27, 1974, p. 297, abstract No. 119104d.
Sheehy et al., Science, vol. 188, No. 4195, Jun. 27, 1975, pp. 1308–1310.

*Primary Examiner*—Benjamin R. Padgett
*Assistant Examiner*—Christine M. Nucker
*Attorney, Agent, or Firm*—Howard W. Bremer

[57] ABSTRACT

A cellular method for typing lymphocyte defined human leukocyte antigens by utilizing human blood leukocytes which have been sensitized to proliferatively respond to the secondary stimulus of the leukocyte antigens to which they have been sensitized. The sensitization is accomplished by incubating, in vitro, in a mixed leukocyte culture, the leukocytes to be sensitized with leukocytes differing by only a single major histocompatibility complex haplotype or a single HLA-D antigenic determinant.

8 Claims, No Drawings

METHOD FOR TYPING HUMAN LEUKOCYTE ANTIGENS

The invention described herein was made in the course of work under a grant or award from the Department of Health, Education, and Welfare.

This is a continuation of application Ser. No. 679,545, filed June 18, 1976, abandoned.

This invention relates to a method for typing or defining human leukocyte antigens.

More specifically, this invention relates to a method for typing or defining human leukocyte antigens which is capable of defining such antigens in both the familial and unrelated population.

This invention also relates to human leukocytes which have been sensitized to respond proliferatively to the secondary stimulus of the leukocyte antigens to which they have been sensitized as a reagent for the typing method.

It is well known that rejection of a transplanted tissue or organ is initiated when the graft recipient's immune system recognizes genetically controlled "foreign" antigens on the grafted tissue; and that in humans a single genetic region called HLA (human leukocyte antigens) or the major histocompatibility complex (MHC), appears to control the majority of strong antigens important in graft rejection.

This invention finds particular application in the "matching" of two individuals where organ or tissue transplantation is contemplated in an effort to minimize the antigenic disparity between the donor and recipient, thereby minimizing the liklihood of rejection of the transplanted organ or tissue.

Two methods are commonly used for detecting antigens associated with the major histocompatibility complex: (i) serological testing for HL-A SD (serologically defined) antigens, and (ii) mixed lymphocyte culture (MLC) test that define disparity at an HL-A LD (lymphocyte defined) locus (or at several loci). In MLC tests, lymphocytes from one individual (the "responder") are cultured for 4 to 7 days with "stimulating" lymphocytes from another individual. To prevent their proliferation, stimulating cells are treated with mitomycin C or x-rays before they are mixed. When the stimulating cells are from unrelated persons or family members whose MHC is different from that of the responder, the untreated lymphocytes proliferate; this proliferation is assayed by incorporation of tritiated thymidine into the proliferating cells. All SD and LD loci are closely linked genetically, and within families they are inherited as a unit called a haplotype. However, since the SD and LD loci are genetically separable, both the serological and MLC tests are necessary in the evaluation of the MHC relationship between two individuals.

In transplants between SD matched persons who are not related, the frequency and severity of rejection generally have been much greater than in transplants between siblings with identical MHC's; moreover, most unrelated individuals who are SD identical are LD disparate when tested by the MLC assay. There is some evidence that MLC matching for HLA LD antigens may be useful for predicting the success of a transplant.

Two major obstacles prevent the widespread use of MLC tests for transplant matching. (i) The result cannot be obtained in less than 4 to 5 days—a time that exceeds the limits for cadaver organ preservation. (ii) Although MLC tests can identify individuals that are matched for their LD antigens, it does not indicate which specific LD antigens the two persons bear; therefore lymphocytes from all potential donors must be tested in MLC with lymphocytes from all potential recipients.

This last problem would be alleviated by an "LD typing" method (analogous to serological typing that has been done for blood groups and HLA SD antigens) that would identify specific LD antigens. Because LD typing would preclude the necessity of blood cells from all potential recipients and donors being present in the same MLC testing laboratory at the same time, the LD type of any potential tissue donor would be determined, and the donor organ or bone marrow could be sent to an LD matched recipient at any center in the world.

The present invention offers a solution to the above problem and provides a method for LD typing which offers substantial advantages over known methods. This method has been designated primed LD typing (hereinafter referred to as PLT) and offers the following significant advantages:

(1) PLT appears to recognize LD;
(2) results are obtained in less than two days and usually within 24 hours;
(3) reagents can be readily produced;
(4) even very rare LD haplotypes can be conveniently typed.

The method of the present invention is based upon the earlier finding that lymphocytes stimulated to proliferation in a primary MLC exhibit an accelerated secondary proliferative response when stimulated 14 days later with leukocytes of the original sensitizing leukocyte donor (see L. C. Anderson and P. Hayry, Eur. J. Immunol. 3, 595 (1973).

It has now been discovered not only that this process could be used for recognizing the HLA-D region antigens of the major histocompatibility complex in man, but that if the leukocytes from a person are stimulated in a primary MLC with leukocytes obtained from a second person who differs from the first person by a single HLA-D antigenic determinant, and probably by only a single MHC haplotype, and the stimulating leukocytes are treated to prevent their proliferation in MLC, a discriminatory type of leukocyte can be obtained which permits LD typing in, not only the familial, but also in the unrelated population via the secondary proliferative response method.

For example, cells (leukocytes) of individual A are "primed" by stimulating them with cells treated with mitomycin C ($B_m$cells) obtained from a person, B, who differs from A by only a single MHC haplotype (for example, a parent or child of A). When the MLC proliferative response is essentially completed (after 9 to 14 days), the cells remaining in the incubation medium are recovered by centrifugation and are used as the PLT cells. These cells are "restimulated" with $B_m$ cells or with cells from any other person who is to be LD typed, and their proliferation is assayed by uptake of tritiated thymidine. On restimulation with $B_m$ cells, or with cells of family members having the same MHC that A recognized on $B_m$, a significant proliferative response is observed after as few as 24 hours. Stimulation by cells of unrelated persons ranges from none to that seen with $B_m$; those persons whose cells restimulate as well as $B_m$ presumably bear LD antigens very similar to those recognized on $B_m$ by A. Thus PLT cells should identify individuals bearing specific LD antigens. Many populations of PLT cells, each specific for antigens of a different LD haplotype, can easily be obtained via primary MLC's with cells from the appropriate members of different families.

The following reagents, media, and techniques were used in establishing the operability of the present invention as hereinafter described. It will be readily evident, however, to those skilled in the art that variations in techniques, times, volumes and types of materials and equipment and in the various media can be used without departing from the teaching and scope of the invention.

MEDIUM AND CELLS

The culture medium was RPMI 1640 with 25 mM HEPES buffer (available from Gibco Diagnostics, catalog No. 240, Madison, Wisconsin) supplemented with penicillin and streptomycin in amounts sufficient to inhibit the growth of extraneous microorganisms in the medium. Plasma pools were from at least 20 donors who had never been transfused, grafted or been pregnant. The plasma was heat inactivated (56° C. for 30 minutes) before use.

Whole heparinized blood was centrifuged (15 minutes, 300 g) to obtain buffy coat cells which were further purified by the Ficoll-Hypaque Technique (Boyum, Scand, J. of Clin. and Lab. Invest., Vol. 21, Supplement 97, pp. 1–91 (1968). Stimulating cells for primary cultures were irradiated (gamma radiation) 4000 r at a dose rate of about 400 r/min).

PRIMARY CULTURES

PLT cells were generated by culturing $1 \times 10^7$ responding cells with $1 \times 10^7$ irradiated (gamma radiation) stimulating cells in Falcon flasks (cat. No. 3013), in 20 ml. of medium containing 5% (v/v) human plasma at 37° C. After 10 days of culturing in a 5% $CO_2$ incubator, nonadherent cells were suspended by vigorous pipetting, centrifuged (15 min., 300 g) and resuspended in fresh medium for counting. Harvested PLT cells were either restimulated or frozen in accordance with the method described below for later use.

SECONDARY CULTURES

Secondary cultures were performed in microtiter plates with V-bottom wells (Linbro, cat. No. IS-MVC-96TC). Viable PLT cells and viable stimulating cells ($2.5 \times 10^4$ and $5 \times 10^4$, respectively) were cultured in each well in 0.15 ml. of medium containing 25% plasma at 37° C. (The stimulating cells were not treated to prevent their proliferation). Total culture time was from about 24 to 48 hours with a 2 $\mu$Ci pulse of tritiated thymidine (Nuclear Chicago, 1.9 Ci/m mole) in 0.05 ml. of medium being added during approximately the last 6 to 12 hours of this time. Cultures were harvested in groups of 24 (cultures were done at least in triplicate) on to glass fiber filters and prepared for liquid scintillation counting (M. L. Bach, et al, Histocompatibility Testing (1970) pp. 643–653, Munksgaard, Copenhagen).

If desired, tritiated uridine can be used instead of tritiated thymidine (Sheehy, et al, Histocompatibility Testing, 1975, Munksgaard, Copenhagen, ed. Kissmeyer-Nielsen, pp. 569–575 (1975).

FREEZING PLT CELLS

Freezing methods are those used for fresh lymphocytes. Freezing medium consisted of 70% medium or PBS, (phosphate buffered saline) 20% heat-in-activated and filtered (0.45$\mu$ millipore) pooled human serum, and 10% dimethyl sulfoxide (DMSO). Cells are suspended in cold freezing medium (4° C.), distributed into Nunc plastic freezing vials in convenient numbers (about $6-20 \times 10^6$ per vial), and placed in a very thin cardboard box or an open container into a $-80°$ C. freezer overnight. Later, vials may be transferred to liquid nitrogen tanks for long-term storage.

Before use, cells are thawed rapidly by shaking vials in a 37° C. water bath until ice is just melted, diluted 3-fold with cold PBS (4° C.), and centrifuged gently (6 minutes, 70 g) to pellet cells. Pellet is resuspended in plasma-supplemented medium for counting and culturing.

Table I below presents the results of one- and two-day restimulation (as counts per minute) of PLT cells from a single family by stimulating cells from members of that family. The number appearing in the columns in Table I are the mean count per minute from triplicate cultures. The data presented were obtained as follows.

Lymphocytes from members of a single family were cultured in four different primary MLC's (Table I). After 13 days, cells from these cultures were restimulated with x-irradiated cells from each of the two parents and six children. The four MHC haplotypes in the family, determined by SD typing, were designated with letters "a" through "d". For each PLT cell (that is, each column of the table), maximum restimulation is caused only by those family members having the haplotype recognized in the primary cultures; cells of other family members restimulated to varying lesser degrees.

That even this lesser stimulation is caused by the MHC is demonstrated in Table I, most clearly in column 7. Although MHC identical to C6, siblings C4 and C5 would be expected to differ from C6 for many of their other loci. Any antigens potentially recognizable by C6 on cells of C4 and C5 must be present on cells of one of the parents. However, lymphocytes primed simultaneously with cells of both parents did not respond to MHC identical siblings. This, with corroborating results from two other families, suggests that non-MHC antigens do not by themselves cause restimulation.

TABLE 1

| Primary MLC | 24-hour PLT | | | 51-hour PLT | | | |
|---|---|---|---|---|---|---|---|
| Responder | C6 = bd* | C5 = bd | F = ab | C6 = bd | C5 = bd | F = ab | C6 = bd |
| Stimulator | F = ab | C3 = bc | C6 = bd | F = ab | C3 = bc | C6 = bd | F + M = ab + cd |
| Haplotype recognized | a | c | d | a | c | d | a + c |
| PLT Stimulators for PLT: | | | | | | | |
| F = ab | 2185 | 239 | 0 | 30875 | 11523 | 0 | 26133 |
| M = cd | 172 | 1863 | 361 | 6356 | 26190 | 7335 | 19779 |
| C1 = ac | 1941 | 1963 | 33 | 28910 | 26744 | 1225 | 30868 |
| C2 = ad | 2326 | 281 | 550 | 29757 | 8427 | 7303 | 24228 |
| C3 = bc | 299 | 1807 | −64 | 6604 | 14999 | 859 | 24599 |
| C4 = bd | 36 | −8 | 455 | −50 | 429 | 6634 | −85 |
| C5 = bd | −26 | 0 | 437 | −265 | 0 | 5354 | −223 |

TABLE 1-continued

| Primary MLC | 24-hour PLT | | | 51-hour PLT | | | |
|---|---|---|---|---|---|---|---|
| Responder | C6 = bd* | C5 = bd | F = ab | C6 = bd | C5 = bd | F = ab | C6 = bd |
| Stimulator | F = ab | C3 = bc | C6 = bd | F = ab | C3 = bc | C6 = bd | F + M = ab + cd |
| Haplotype recognized | a | c | d | a | c | d | a + c |
| C6 = bd | 0+ | 39 | 565 | 0 | 349 | 7390 | 0 |

*Family members are designated by capital letters, and their MHC haplotypes by lowercase letters. For example, child C6 has MHC haplotypes b and d.

+For this column, restimulation (counts per minute) by C6, who was the responder in the primary culture, was subtracted from all numbers in the column. These "background" counts, ranging from 307 to 733 for the seven columns, were subtracted from all numbers in each column.

As has been pointed out hereinbefore, the LD typing method of this invention is applicable not only in the familial but also in the unrelated population. This is evidenced by the experiment described below, which is based upon the hypothesis that since siblings sharing a single MHC haplotype stimulate each other less on the average in a standard MHC than siblings differing for both MHC hyplotypes, unrelated persons postulated to share LD antigens by PLT testing should stimulate each other less on the average in a standard MLC than persons who do not share LD. Results are presented in Table 2.

Lymphocytes from a family were used to prepare PLT cells for all four of the family's MHC haplotypes. For example, PLT cells from a primary culture with the mother as responder (haplotypes y and z) and a son Fred as stimulator (haplotypes w and y) were used to define the LD antigens of haplotype w. PLT cells prepared by using Fred as responder and the mother as stimulator defined LD antigens of haplotype z. Cells from 11 unrelated persons were tested as stimulators in the PLT test; restimulation by these cells was 3 to 104 percent of that elicited by cells from the specific family member who was the stimulator in the primary culture. Unrelated persons were arbitrarily considered highly cross-reactive for a given LD haplotype if they restimulated at least 80 percent as much as the average for family members known to have the specific haplotype.

Table 2 shows the average stimulation (counts per minute) in standard MLC's of family responders by unrelated persons cross-reacting highly with both or one of the responder's LD haplotypes or showing no cross-reaction. For each responder, the 11 unrelated stimulators were each placed in one of the three categories indicated. The first column of figures, for example, shows the average response of the father to unrelated persons "highly cross-reactive" in PLT tests defining antigens of (i) both haplotypes w and x, (ii) haplotype w or x but not both, and (iii) neither w or x. Numbers in parentheses are numbers of stimulators included in the calculation of each average.

TABLE 2

| Number of responder's LD haplotypes, with which stimulator cross-reacts highly | Stimulation (count/min) of family responders, and responder's LD haplotypes | | | |
|---|---|---|---|---|
| | Father wx | Fred wy | Bill wz | Mother yz |
| Both | 3311(1) | 8857(1) | 2139(1) | |
| One | 9390(4) | 13136(3) | 4879(3) | 4783(4) |
| None | 13529(6) | 15653(7) | 9607(7) | 10771(7) |

For each family member the trend of MLC response magnitudes is in the predicted direction: Those persons that are highly cross-reactive by PLT for both LD haplotypes of a particular responder stimulate that responder the least. Similarly those that are highly cross-reactive with one haplotype stimulate less than those which do not cross-react highly with either haplotype. The probability of finding this consistent trend by chance alone is less than 0.0025. It is important to note that the observed low stimulation in the standard primary MLC by certain unrelated individuals "highly cross-reactive" for one or two LD haplotypes was predicted from the high stimulation by those same individuals in specific secondary MLC combinations (PLT tests).

As a further test of the ability to do LD typing by the method of this invention, two groups of three unrelated persons were chosen by PLT criteria. One group consisted of three persons that were all "highly cross-reactive" for one LD haplotype, and the other three persons were "highly cross-reactive" for a different LD haplotye. Standard MLC tests were done between all possible pairs from these six persons. The average MLC (in counts per minute) when responder and stimulator were from opposite groups was 7550; the average when responder and stimulator were from the same group was only 5154, about two-thirds as great. This difference was highly significant (P<0.001), demonstrating that, on the average, individuals shared more LD antigens with persons in their own group. These results, and those in Table 2, show that the present method does identify cell components that cause MLC stimulation—that is, that it does type for LD antigens.

Because of the rapidity of the method, and the ease of obtaining PLT cells, the PLT test can easily be applied in an international LD typing program. PLT cells for any LD antigen can be obtained, with the use of cells from appropriate members of any family in which that antigen is found.

Moreover, since fresh PLT cells and those preserved by freezing, for example, by the freezing method described hereinbefore have been found to give quantitatively similar results, it is possible to prepare typing trays that contain frozen PLT cells defining many different LD antigens. The LD type of any person could be rapidly determined by stimulation of the different PLT cells in this panel.

The ability to identify LD antigens may be important in other ways besides its obvious application to transplant matching. LD antigens are controlled by the same region of the MHC that controls the magnitude of immune responses to certain specific antigens. Moreover, the LD region has been associated with susceptibility to oncogenic viral infections in the mouse, and certain LD antigens have been associated with disease of immune etiology in man. Thus PLT may be an important criterion for diagnosing human disease, as well as a specific probe allowing greater understanding of the function and genetic fine structure of the MHC in man and in other species.

It will be evident to the skilled in the art that the aforedescribed procedures and the present invention will also be applicable to cells with different D-locus specificities.

In addition, it seems reasonable to presume that the PLT approach will be usable in the typing of other than HLA-D antigens for diagnostic purposes.

An even more detailed description of the present invention can be found in Science, Vol. 188, pp. 1308–1310, 27 June 1975.

Having thus described the invention, what is claimed is:

1. A method for typing human leukocyte antigens of HLA-D which comprises:
    incubating, in vitro, purified human blood leukocytes obtained from two individuals, where the leukocytes from one of the individuals have been treated to prevent their proliferation during incubation;
    carrying out the incubation for a period of from about 9 to about 14 days to essential completion of the proliferative response;
    recovering the leukocytes from the incubation medium;
    incubating, in vitro, the thus recovered leukocytes, with purified human blood leukocytes obtained from a third individual;
    measuring the response of the recovered leukocytes through the uptake by the responding leukocytes of tritiated thymidine or tritiated uridine added to the incubating mixture; and
    utilizing said measurement as a definition of the antigens present in the third individual.

2. The method of claim 1 wherein the leukocytes of one of the first two individuals differs from those of the other individual by only a single major histocompatibility complex haplotype.

3. The method of claim 1 wherein the treatment of the leukocytes to prevent proliferation during incubation comprises exposure of the leukocytes to gamma radiation.

4. The method of claim 1 wherein the treatment of the leukocytes to prevent proliferation during incubation comprises contacting the leukocytes with mitomycin C.

5. The method of claim 1 wherein the leukocytes obtained from the third individual have been treated to prevent their proliferation during incubation.

6. The method of claim 1 wherein the initial incubation is terminated at 10 days.

7. A reagent for lymphocyte defined typing of human leukocyte antigens which comprises human blood leukocytes which have been sensitized to proliferatively respond to the secondary stimulus of the leukocyte antigens to which they have been sensitized, said sensitization being accomplished by incubating, in vitro, the leukocytes to be sensitized with leukocytes of different LD haplotypes.

8. The reagent according to claim 7 in which the sensitization is accomplished by incubating, in vitro, the leukocytes to be sensitized with leukocytes differing by only a single major histocompatibility complex haplotype.

* * * * *